Figure 1A:
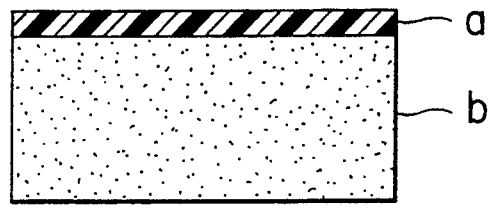

United States Patent [19]

Jalonen et al.

[11] Patent Number: 5,438,067
[45] Date of Patent: Aug. 1, 1995

[54] MEDETOMIDINE PREPARATIONS FOR TRANSDERMAL ADMINISTRATION

[75] Inventors: Harry Jalonen, Turku; Arto Karjalainen, Oulu, both of Finland

[73] Assignee: Orion-yhtymä Oy, Espoo, Finland

[21] Appl. No.: 146,201

[22] Filed: Nov. 12, 1993

[30] Foreign Application Priority Data

May 31, 1991 [GB] United Kingdom ............. 9111732.5

[51] Int. Cl.⁶ .................. A61L 15/44; A61K 9/70; A61F 13/00; A61F 13/02
[52] U.S. Cl. .................... 514/396; 424/447; 424/448; 424/449
[58] Field of Search ................. 424/447, 448, 449; 514/396

[56] References Cited

U.S. PATENT DOCUMENTS 4,783,477 11/1988 Lammintausta et al. .......... 514/396
5,124,157 6/1992 Colley et al. .................. 424/449
5,217,718 6/1993 Colley et al. .................. 424/449

FOREIGN PATENT DOCUMENTS 0072615 2/1983 European Pat. Off. .
0270267 6/1988 European Pat. Off. .
0300652 1/1989 European Pat. Off. .
0331374 9/1989 European Pat. Off. .
0413487 2/1991 European Pat. Off. .
0437030 7/1991 European Pat. Off. .

*Primary Examiner*—Ronald W. Griffin
*Attorney, Agent, or Firm*—Burns, Doane, Swecker & Mathis

[57] ABSTRACT

Salts of medetomidine and optically active enantiomers, thereof, particularly the d-enantiomer are disclosed. These salts may be used to regulate the rate of the transdermal administration of active drugs. The transdermal delivery system comprises a drug impermeable backing layer and an adhesive layer wherein the medetomidine is dispersed throughout the adhesive layer.

17 Claims, 2 Drawing Sheets

MEDETOMIDINE PREPARATIONS FOR TRANSDERMAL ADMINISTRATION

This invention relates to the use of certain salts of medetomidine and its optically active enantiomers, particularly its d-enantiomer, to regulate the rate of the transdermal administration of the drugs.

Medetomidine or 4-[α-methyl-2,3-dimethylbenzyl]-1H-imidazole which has the formula

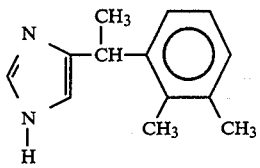

is a well-known $\alpha_2$-adrenoceptor agonist. It has been disclosed in EP 72615 as an antihypertensive agent and in U.S. Pat No. 4783477 as a veterinary sedative-analgesic for small animals. EP 270267 discloses the use of medetomidine in the treatment of anxiety disorders. EP 300652 discloses the optically active enantiomers of medetomidine. Particularly the denantiomer, the generic name of which is dexmedetomidine, is a very selective and potent $\alpha_2$-adrenoceptor agohist. EP 331374 discloses the perioperative use of medetomidine and dexmedetomidine as anaesthetic adjuvants.

In many therapeutical uses a steady, uniform administration of the active agent is desirable. Many compounds are known to have a rather poor bioavailability due to extensive initial metabolism of the drug. Such compounds would not therefore be suitable for oral administration. In many fields of therapy injections are, however, not convenient. Transdermal administration is one alternative in such cases as it combines the convenience of oral administration and the high bioavaiability of injections.

For many different pharmacokinetic and pharmacologigal reasons, only a minor proportion of commercially available therapeutically active substances is suitable for transdermal administration due to many different pharmacokinetic and pharmacological reasons. One of the most limiting factors is, however, the physicochemical properties of the therapeutically active substance itself. For a compound to be able to penetrate the skin it must have both lipophilic (fat soluble) and hydrophilic (water soluble) properties in a suitable proportion. Such a suitable ratio between the lipophilic and hydrophilic properties is not very common for drug substances. The ability of a drug to penetrate through the skin can be predicted by its apparent partition coefficient P' in octanol/water. It is known that compounds having an optimal partition coefficient penetrates the skin better than compounds with either higher or lower partition coefficients. This optimal partition coefficient value is different for different kinds of compounds.

Medetomidine and its optically active enantiomers have proved to possess optimal partition coefficients thus rendering them suitable for transdermal administration.

Figure 1B:
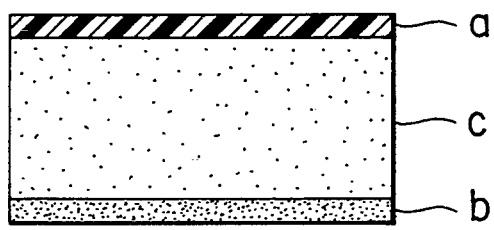
Figure 1C:
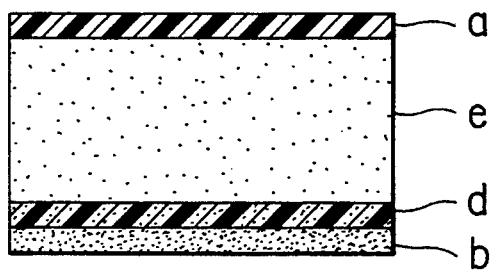

FIGS. 1A, 1B, and 1C show configurations of three types of transdermal delivery system.

Figure 2:
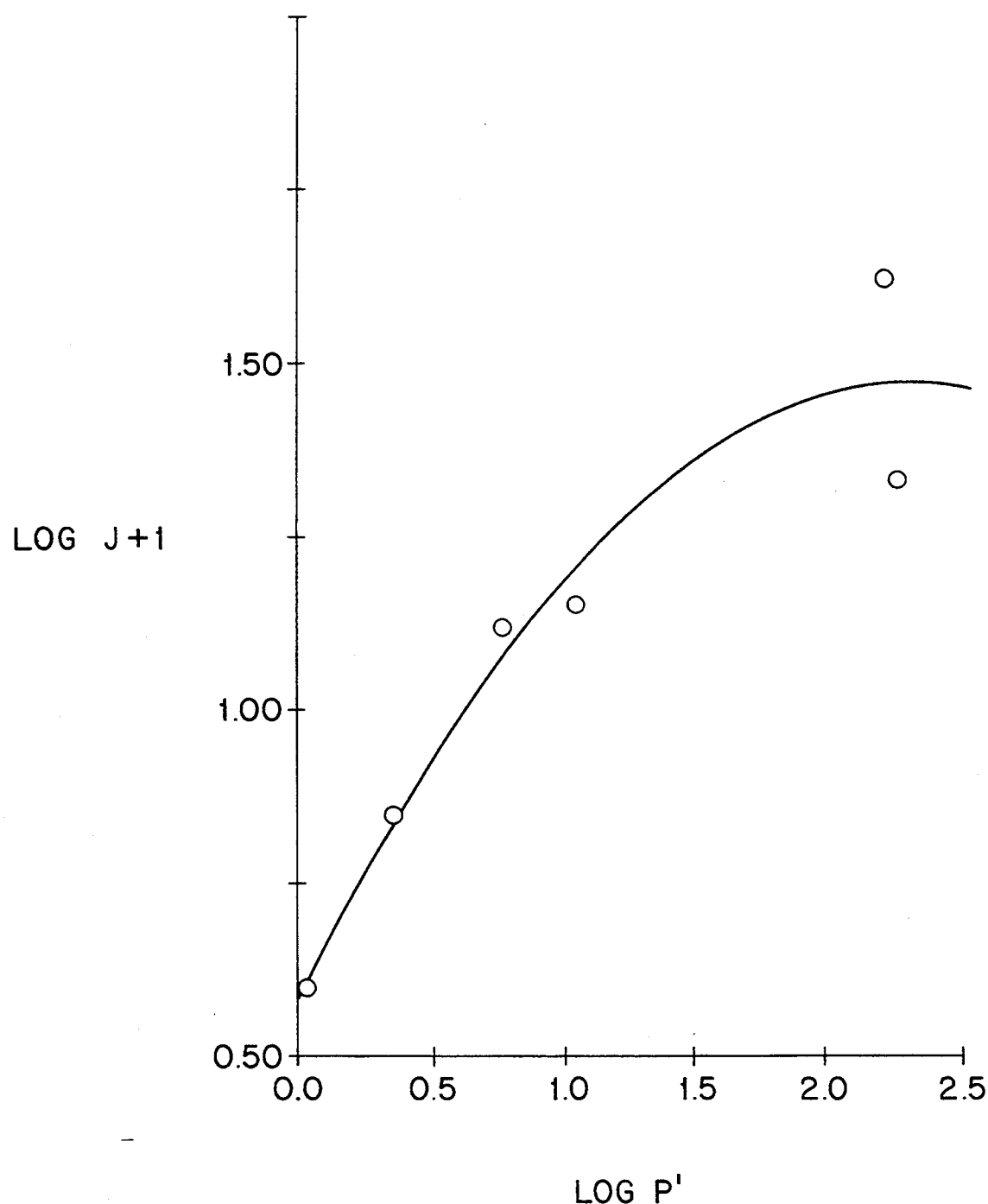

FIG. 2 shows a relationship between the partition coefficient and flux through the skin.

The transdermal administration of the compounds medetomidine and its optically active enantiomers can be accomplished in two different ways: (i) by mixing the therapeutically active compounds with suitable pharmaceutical carriers and optionally penetration enhancers to form ointments, emulsions, lotions, solutions, creams, gels, patches or the like, where preferably a fixed amount of said preparation is to be applied onto a certain area of skin, or (ii) by incorporating the therapeutically active substance into a transdermal delivery system according to one of the alternatives disclosed in FIG. 1. Transdermal drug delivery devices can be categorized into three general types FIGS. 1A, 1B, and 1C. FIG. 1A discloses a transdermal device comprising (a) a drug impermeable backing layer and (b) a adhesive layer that fixes the bandage to the skin. In this preparation the drug is mixed in the adhesive layer. FIG. 1B represents a device incorporating a backing layer (a), an adhesive layer (b) and a matrix layer (c) preferably made of a polymer material in which the drug is dispersed. The rate at which the drug is released from the device is here controlled by the polymer matrix. A third kind of device is the reservoir system according to FIG. 1C comprising (a) a drug impermeable backing layer; an adhesive layer (b); a drug permeable membrane (d) positioned relative to said backing layer so that at least one drug reservoir compartment is defined between said membrane and said backing layer, and (e) a drug or composition thereof within said drug reservoir. In this case the drug in the reservoir is usually in liquid or gel form. The drug permeable membrane controls the rate at which the drug-is delivered to the skin.

By the term "suitable pharmaceutical carrier" is meant a non-toxic pharmaceutically acceptable vehicle including for example polyethylene glycol, propylene glycol, isopropanol, ethanol, oleic acid, N-methylpyrrolidone, sesame oil, olive oil, wood alcohol ointments, vaseline and paraffin or a mixture thereof.

Suitable penetration enhancers include for example saturated and unsaturated fatty acids and their esters, alcohols, monoglycerides, diethanolamines, N,N-dimethylamines such as linolenic acid, linolenyl alcohol, oleic acid, oleyl alcohol, stearic acid, stearyl alcohol, palmitic acid, palmityl alcohol, myristic acid, myristyl alcohol, 1-dodecanol, 2-dodecanol, lauric acid, decanol, captic acid, octanol, caprylic acid, 1-dodecylazacycloheptan-2-one sold under the trademark AZONE, ethyl caprylate, isopropyl myristate, hexamethylene lauramide, hexamethylene palmirate, capryl alcohol, decyl methyl sulfoxide, dimethyl sulfoxide, salicylic acid and its derivatives, N,N-diethyl-m-toluamide, crotamiton, 1-substituted azacycloalkan-2-ones, polyethylene glycol monolaurate and any other compounds compatible with medetomidine and its optically active enantiomers and the packages and having transdermal permeation enhancing activity.

The preferred administration rates of the drug is 0.1–1000 μg/h through a skin area of about 2–90 $cm^2$, preferably 10–30 $cm^2$. The amount of drug delivered into the skin can be controlled by a number of factors including skin patch size, degree of drug loading, the use of rate controlling membranes, permeation enhancers etc.

The backing layer can be flexible or nonflexible and suitable materials include for example cellophane, cellulose acetate, ethylcellulose, vinylacetate-vinylchloride copolymers, polyethylene terephthalate, nylon, polyethylene, polypropylene, polyester films, polyvinylidene chloride, coated flexible fibrous backings such as paper and cloth and aluminium foil.

The adhesive layer comprises for example polysiloxanes, polyisobutylenes, polyacrylates, polyurethanes, ethylene-vinyl acetate copolymers, polyether amide block polymers, polyisobutene, polystyrene-isoprene copolymers, polystyrene-butadiene copolymers. Preferred adhesives are acrylates, silicones and polyurethanes.

The drug permeable membrane can be made of materials including polyethylene, polypropylene, ethylene vinyl acetate copolymers, polycarbonates, polyvinyl chloride, polyacrylate polymers, polysulfone polymers, polyvinylidienes, polyvinylidenes, polyesters and polyisobutylenes, for example.

The matrix is preferably an anhydrous matrix such as natural or synthetic rubbers or other polymeric material, thickened mineral oil or petroleum jelly, for example. Preferred embodiments are ethylene/vinylacetate copolymers, silicones or polyurethanes.

EP 413487 discloses a transdermal device of dexmedetomidine. In this publication it is said that the base form is more preferable than the acid addition salts. Various organic and inorganic salts were listed. The salt mentioned were, however, all hydrophilic salts, i.e. salts of inorganic acids and and organic acids with short alkyl chains. The situation is different for salts of carboxylic acids with long alkyl chains such as decanoate i.e. salts of carboxylic acids of 5 to 16 carbon atoms, which contain an aliphatic chain of at least 5 carbon atoms. Such salts were not mentioned in the list of salts in EP 413487. Our experiments show that the permeation of medetomidine decanoate from a hydrophilic vehicle such as ethanol: water is essentially higher than the permeation for the base and the hydrophilic salts of inorganic acids and short chained organic acids such as acetate and propionate.

On the other hand we have surprisingly found that the hydrophilic salts of medetomidine such as short chained carboxylic acids, particularly acetate and propionate, exhibit an excellent permeation from a lipophilic vehicle such as isopropyl myristate. The flux of both these both salts is far higher than for the base or for the decanoate.

EXPERIMENTS

Preparation of the medetomidine salts

Equivalent amounts of medetomidine base and acid in an ethanolic solution were stirred for 2 hours at 40° C. The ethanol was evaporated and the salts were crystallized from different mixtures of toluene and acetone or dichlormethane and hexane.

TABLE I

Melting points of medetomidine salts

| Salt | Melting point °C. |
|---|---|
| citrate | about 54 |
| HCl | about 168, 177 |
| acetate | about 90 |
| propionate | about 65 |
| decanoate | amorphous |
| free base | about 108 |

Analytical HPLC method

The fully automated (Hewlett-Packard, USA) liquid chromatograph consisted of a pump 1090, an autosampler and autoinjector (79847A) and a fixed wavelength UV detector, 210 nm (79881A). The chromatograms, retention times and peak areas were recorded with an integrator 3393. The separations were carried out at a column temperature of 37° C. on a 35 * 4.6 mn stainless steel column (packed with a 3-$\mu$m spherical octadecylsilane-bonded silica particles; HS-3 C-18, (Perkin-Elmer, USA). The mobile phase consisted of different mixtures of acetonitrile: 0.05M aqueous phosphate buffer pH 7.4 containing 0.004M of dimethyloctyl amine. The flow rate was 0.8 ml/min.

Shake-flask apparent partition coefficient method

The apparent partition coefficients for the different salts of medetomidine were determined by dissolving the salts in octanol-saturated water using as a modified method the one described for clonidine and structurally related imidazoles (Timmermans et al Naunyn-Schmid. Arch. Pharmacol. 300, p. 217, 1977) the starting concentration in the aqueous phase being 200 $\mu$M. The aqueous phase was shaken with water-saturated n-octanol (the volumes for aqueous phase to octanol being either 10:1 or 20:1) for one hour at room temperature (20°–22° C.) and then equilibrated by allowing to stand for 20 hours. At least three parallel tests were made in each case. Samples were taken from the aqueous phase and the concentration of the compound was analyzed according to the HPLC method described above. The apparent partition coefficient (P') can be calculated from the equation:

$$P' = (C_0 - C_1) V_{Aq}/C_1 V_{Oct}$$

$C_0$ is the initial and $C_1$ is the final (after partioning) concentration of the tested compound in the aqueous phase. $V_{Aq}$ and $V_{Oct}$ are the volumes of the aqueous and the octanol phases respectively.

IN VITRO SKIN PERMEATION MEASUREMENTS

Treatment of skin samples

All of the penetration and skin/solvent partition experiments reported here utilized human skin from the thigh region obtained at autopsy. The skin samples (with the thickness of about 1 mm) containing the epidermis and a part of dermis were taken with a dermatome (Elemo HM94, Switzerland). The epidermis was separated from the dermis by the method of Chandrasekaran et al (Am.I.Chem.Eng.J. 22 p.828, 1976) by keeping the skin in hot water (60° C.) for 60 seconds. After isolation the epidermis was dried between two sheets of paper, cut into smaller pieces and stored in aluminium foil in polyethylene bags at 4° C. for no more than 4 weeks.

Permeation experiments

Vertical Franz type of diffusion cells were used in the experiments (Franz, Curr. Probl. Dermatol. 7, p.58, 1978), (FDC-400, diffusion area 1.77 cm², receiver compartment volume 11.5–12.0 ml, Crown Glass Company, Inc. USA). The stirring (500 rpm) of the magnet bar was generated for the cells with a drive console (VSC-1, Crown Glass Company Inc. USA). The cells were made of glass and were jacketed for temperature control 37° C. (MGW Lauda, type MS, Germany).

The stored skin (epidermis) samples were checked visually and microscopically for defects before use. In the permeation experiment the epidermis sample was clamped between the two parts of the cell system. To be able to prevent any leakages the four corners of the epidermis sample extended outside the contact area of the system. The epidermis sample was hydrated from both sides over night, with aqueous phosphate buffer 0.05 M pH 7.4 (6.9 g $NaH_2PO_4*H_2O/1$ of water, pH adjusted to 7.4 with 10 M NaOH) on the receiver side (viable epidermis side) and on the donor side (stratum corneum side) with the same solvent, ointment or patch (without the penerrant) that was going to be used as the donor formulation of the penerrant in the actual skin permeation experiment. Next morning after hydrating the skin overnight the permeation experiment started by first removing the donor formulation and the receiver solutions from the diffusion cell: fresh aqueous phosphate buffer pH 7.4 was added to the receiver side (11.5 ml) and a formulation volume now containing a known amount of penerrant molecule was added to the donor side. Particular care was taken to prevent air bubbles from forming on the surface of the skin. Samples of 0.4 ml were withdrawn from the receiver chamber at intervals and replaced with the same volume of fresh receiver solution.

The samples were then analyzed according to the HPLC method described above. Corrections were made (for the losses from earlier samplings) in calculating the cumulative amount of drug that permeated the skin.

The permeation of the penerrant through epidermis was described by a plot of cumulated amount of penerrant Q (in μg) vs time in hours. The slope of the curve and the intercept on the x-axis (lag time) were determined by linear regression. Penerrant flux J (in $\mu g/cm^2 h$) was calculated from the slope μg penetrant/h and knowing the area of the skin surface through which diffusion was taking place ($cm^2$) (Flynn et al, CRC Press, Boca Raton, Florida, p. 45, 1987). The permeability constant $k_p$ was calculated from the formula $k_p = J/C$ where J represents the steady-state flux end C the donor concentrations. The results are presented in Tables II to V.

TABLE II

Permeation of different salts of medetomidine through human cadaver epidermis at 37° C. from EtOH:H$_2$O 1:1 solution, concentration of all salts 5 mg/ml calculated as base, receptor solution phosphate buffer pH 7.4.

| Salt | pH of solution | Degree of saturation % | Flux ± SD μg/cm² h | Log P' | $k_p*10^{-3}$ cm/h |
|---|---|---|---|---|---|
| HCl | 4.4 | 1 | 0.4 ±0.1 | 0.03 | 0.09 |
| Citrate 0.5 eqv. | 5.8 | 1 | 0.7 ±0.2 | 0.35 | 0.1 |
| Acetate | 6.3 | 1 | 1.3 ±0.4 | 0.76 | 0.26 |
| Propionate | 6.4 | 0 | 1.4 ±0.1 | 1.05 | 0.27 |
| Decanoate | 6.4 | 12 | 4.1 ±0.2 | 2.21 | 0.81 |
| Base | 8.0 | 8 | 2.1 ±0.2 | 2.26 | 0.42 |

The difference between the flux values of all pairs of salts is statistically significant (P < 0.05)

The parabolical relationship between flux and partition coefficient for the six different salt forms is illustrated by FIG. 2 and the formula $$\log(J)+1 = -0.164*(\log P')^2 + 0.757*(\log P')+0.589$$

n=6; r=0.961; P<0.021

The flux through the skin seemed to be governed by the partitioning coefficient and a maximum is found near log P'=2.2 which is earlier reported as the optimum range for skin permeation (Guy etal, Pharm. Res. 5, p. 753, 1988). The parabolic relationship between the skin permeation and the partition coefficient of the penetrant has been earlier reported for drugs and other compounds by Lien et al, J. Soc. Cosmet. Chem. 24, p. 371, 1973; Michaels etal, AIChE J. 21, p. 985, 1975 and Hoelgaard et al, J. Contr. Rei. 2, p. 111, 1985.

FIG. 2 discloses that the medetomidine salts resulting in the same or a better flux than the free base are found in the log P'-range 1.2 to 3.4 (in octanol/water). This range represents salts having an optimal lipophilicity and they are salts of lipophilic carboxylic acids of 4 to 16 carbon atoms.

TABLE III

Effect of ethanol concentration in the donor solution on the percutaneous absorption of medetomidine base and decanoate at 37° C.

| Donor solution EtOH:H$_2$O | Salt | Conc. as base mg/ml | pH | Flux ± SD μg/cm² h | $k_p*10^{-3}$ cm/h |
|---|---|---|---|---|---|
| 0:100 | Decan. | 0.44 | 6.4 | 2.5 ±0.5 | 5.6 |
| 0:100 | Base | 0.32 | 7.7 | 1.6 ±0.0 | 5.2 |
| 20:80 | Decan. | 2.08 | 6.2 | 6.9 ±0.7 | 3.3 |
| 20:80 | Base | 1.40 | 8.2 | 4.2 ±0.3 | 3.0 |
| 50:50 | Decan. | 42.05 | 6.4 | 26.7 ±0.7 | 0.6 |
| 50:50 | Base | 63.17 | 8.1 | 23.1 ±0.5 | 0.4 |
| 100:0 | Decan. | 79.03 | | 35.0* ±14.0 | 0.4 |
| 100:0 | Base | 92.00 | | 17.2* ±3.3 | 0.2 |

*The difference between the flux values is statistically significant (P < 0.05).

TABLE IV

Effect of different salts of medetomidine on the percutaneous flux and permeability constant through human cadaver epidermis at 37° C. from saturated isopropylmyristate donor solutions.

| Salt | Conc. calc. as base mg/ml | Flux ± SD μg/cm² h | $k_p*10^{-3}$ cm/h |
|---|---|---|---|
| Decanoate | 169.96 | 2.6 ±0.2 | 0.02 |
| Propionate | 225.55 | 24.0 ±5.9 | 0.11 |
| Base | 5.27 | 5.2 ±1.0 | 0.99 |
| Acetate | 27.30 | 54.2 ±11.7 | 1.99 |

The differenc between all flux values (with the exception of the comparison of the pair decanoate and base) is statistically significant (P < 0.05).

TABLE V

Percutaneous absorption rate of medetomidine base and decanoate through cadaver epidermis at 37° C. from buffered aqueous solutions.

| Donor solution pH | Salt | Conc. calc. as base mg/ml | Flux ± SD μg/cm² h | $k_p*10^{-3}$ cm/h |
|---|---|---|---|---|
| 5.0 | Decan. | 3.516 | 0.51 ±0.05 | 0.15 |
| 5.0 | Base | 3.200 | 0.09 ±0.01 | 0.03 |

TABLE V-continued

Percutaneous absorption rate of medetomidine base and decanoate through cadaver epidermis at 37° C. from buffered aqueous solutions.

| Donor solution pH | Salt | Conc. calc. as base mg/ml | Flux ± SD μg/cm² h | $k_p*10^{-3}$ cm/h |
|---|---|---|---|---|
| 7.4 | Decan | 0.309 | 1.04 ±0.03 | 3.35 |
| 7.4 | Base | 0.272 | 0.60 ±0.04 | 2.20 |
| 7.4 + 0.3 mg/ml decanoic acid | Base | 0.276 | 0.80 ±0.14 | 2.91 |

The difference between all pairs of flux values (with the exception of the comparison of the pair of decanoate pH 5 and base pH 7.4) is statistically significant ($P < 0.05$).

TABLE VI

Effect of pH of the donor solution on the percutaneous penetration of medetomidine through human cadaver epidermis at 37° C.

| pH | Conc. mg/ml | Ioniz. degree % | Flux ± SD μg/cm² h | $k_p*10^{-4}$ cm/h | Enhanc. factor | Log P' |
|---|---|---|---|---|---|---|
| 3.0 | 130.00 | 100.0 | 0.22 ±0.04 | 0.02 | 1 | −0.42 |
| 5.1 | 11.06 | 99.1 | 0.43 ±0.14 | 0.39 | 23 | 0.88 |
| 6.9 | 1.00 | 62.4 | 1.34 ±0.39 | 13.36 | 775 | nd |
| 8.9 | 0.43 | 1.6 | 1.41 ±0.30 | 32.59 | 1891 | 3.08 |

We claim:

1. A transdermal preparation comprising a lipophilic salt of medetomidine or its optically ;active enantiomer with a carboxylic acid of 5 to 16 carbon atoms containing an aliphatic chain of at least 5 carbon atoms, as an active ingredient and a hydrophilic water soluble vehicle.

2. A preparation according to claim 1 where the salt is decanoate.

3. A preparation according to claim 1 where the hydrophilic vehicle is an ethanol-water mixture.

4. A preparation according to claim 1 which is in the form of an ointment, emulsion, lotion, solution, gel or cream.

5. A preparation according to claim 1 where the preparation is a transdermal delivery system comprising a drug impermeable backing layer and an adhesive layer where the active ingredient is dispersed in the adhesive layer.

6. A preparation according to claim 1 where the preparation is a transdermal delivery system comprising a drug impermeable backing layer; an adhesive layer and a matrix layer in which the active ingredient is dispersed.

7. A preparation according to claim 6 where the matrix layer is made of a poller material.

8. A preparation according to claim 1 where the preparation is a transdermal delivery system comprising a drug impermeable backing layer; an adhesive layer; a drug permeable membrane positioned relative to said backing layer so that at least one drug reservoir compartment is defined between said membrane and said backing layer and a drug or composition thereof within said drug reservoir.

9. A transdermal preparation comprising a hydrophilic salt of medetomidine or its optically active enantiomer, said salt having a logarithmic value for the apparent partition coefficient in the range 0.2–1.5 in octanol/water, as an active ingredient and a lipophilic fat soluble vehicle.

10. A preparation according to claim 9 where the lipophilic vehicle is isopropyl myristate.

11. A preparation according to claim 9 which is in the form of an ointment, emulsion, lotion, solution, gel or cream.

12. A preparation according to claim 9 where the preparation is a transdermal delivery system comprising a drug impermeable backing layer and an adhesive layer where the active ingredient is dispersed in the adhesive layer.

13. A preparation according to claim 9 where the preparation is a transdermal delivery system comprising a drug impermeable backing layer; an adhesive layer and a matrix layer in which the active ingredient is dispersed.

14. A preparation according to claim 13 where the matrix layer is made of a polymer material.

15. A preparation according to claim 9 where the preparation is a transdermal delivery system comprising a drug impermeable backing layer; an adhesive layer; a drug permeable membrane positioned relative to said backing layer so that at least one drug reservoir compartment is defined between said membrane and said backing layer and a drug or composition thereof within said drug reservoir.

16. A salt of medetomidine or an optically active enantiomer thereof with a C5 to C16 carboxylic acid compound containing an aliphatic chain of at least 5 carbon atoms.

17. The decanoate of medetomidine or an optically active enantiomer thereof.

* * * * *